United States Patent
Lee et al.

(10) Patent No.: US 9,470,677 B2
(45) Date of Patent: Oct. 18, 2016

(54) CELL WITH SURFACE COATED WITH ANXA1 AND USE THEREOF

(71) Applicant: Samsung Electronics Co., Ltd., Suwon-si, Gyeonggi-do (KR)

(72) Inventors: Jungmin Lee, Seoul (KR); Jae Il Lee, Yongin-si (KR); Soshin Ahn, Seoul (KR); Hye Yoon Kang, Suwon-si (KR)

(73) Assignee: SAMSUNG ELECTRONICS CO., LTD., Suwon-Si (KR)

( * ) Notice: Subject to any disclaimer, the term of this patent is extended or adjusted under 35 U.S.C. 154(b) by 0 days.

(21) Appl. No.: 14/554,955

(22) Filed: Nov. 26, 2014

(65) Prior Publication Data
US 2015/0148253 A1     May 28, 2015

(30) Foreign Application Priority Data
Nov. 28, 2013   (KR) .................. 10-2013-0146224

(51) Int. Cl.
*G01N 33/574*     (2006.01)
*G01N 33/50*      (2006.01)

(52) U.S. Cl.
CPC ....... *G01N 33/502* (2013.01); *G01N 2333/705* (2013.01); *G01N 2500/10* (2013.01)

(58) Field of Classification Search
CPC ................... G01N 33/502; G01N 2333/705; G01N 2500/10
USPC .......................................................... 506/9
See application file for complete search history.

(56) References Cited

U.S. PATENT DOCUMENTS

| 2010/0233160 A1 | 9/2010 | Schrattenholz |
| 2010/0331192 A1 | 12/2010 | Zha et al. |
| 2012/0003299 A1* | 1/2012 | Kawakami ........... A61K 9/0019 424/450 |

FOREIGN PATENT DOCUMENTS

| KR | 20030086551 A | 11/2003 |
| KR | 20090029868 A | 3/2009 |
| WO | 2011/154705 A1 | 12/2011 |

OTHER PUBLICATIONS

Solito et al., Journal of Immunology, 2000, 165, pp. 1573-1581.*
Kim et al., Nephron, 1996, 74, pp. 39-44.*
Dorovkov et al., "Phosphorylation of Annexin A1 by TRPM7 Kinase: A Switch Regulating the Induction of an α-Helix", *Biochemistry*, 50: 2187-2193 (2011).
Gerke et al., "Annexins: From Structure to Function", *Physiol. Rev.*, 82: 331-371 (2002).
Hatakeyama et al., "Targeted drug delivery to tumor vasculature by a carbohydrate mimetic peptide", *PNAS*, 108(49): 19587-19592 (2011).

(Continued)

*Primary Examiner* — Larry Riggs
*Assistant Examiner* — Karla Dines
(74) *Attorney, Agent, or Firm* — Leydig, Voit & Mayer, Ltd.

(57) ABSTRACT

A cell having a surface coated with Annexin A1 (ANXA1), a method of detecting a substance binding to ANXA1 using the cell, and a method of preparing the cell are provided.

3 Claims, 3 Drawing Sheets

(56) References Cited

OTHER PUBLICATIONS

Oh et al., "Subtractive proteomic mapping of the endothelial surface in lung and solid tumours for tissue-specific therapy", Nature, 429: 629-635 (2004).

Rescher et al., "Annexins—unique membrane binding proteins with diverse functions", Journal of Cell Science, 117 (13), 2631-2639 (2004).

Solito et al., "Post-translational modification plays an essential role in the translocation of annexin A1 from the cytoplasm to the cell surface", *FASEB J*, 20(9): 1498-1500 (2006).

Ter-Avanesyan et al., "Development of yeast surface display system and its application to biocatalysis", Korea Research Institute of Bioscience and Biotechnology, Research Study, dated Sep. 2000, downloaded from <<http://report.ndsl.kr/repDetail.do?cn=TRKO200200050614#>> on Jan. 23, 2015.

* cited by examiner

Cell-ELISA signal Comparison

1) Without exogenous ANXA1 coating

2) With exogenous ANXA1 coating

SEQUENCE LISTING

```
<160> NUMBER OF SEQ ID NOS: 2

<210> SEQ ID NO 1
<211> LENGTH: 346
<212> TYPE: PRT
<213> ORGANISM: Artificial Sequence
<220> FEATURE:
<223> OTHER INFORMATION: Synthetic (annexin A1 [Homo sapiens])

<400> SEQUENCE: 1

Met Ala Met Val Ser Glu Phe Leu Lys Gln Ala Trp Phe Ile Glu Asn
1               5                   10                  15

Glu Glu Gln Glu Tyr Val Gln Thr Val Lys Ser Ser Lys Gly Gly Pro
                20                  25                  30

Gly Ser Ala Val Ser Pro Tyr Pro Thr Phe Asn Pro Ser Ser Asp Val
            35                  40                  45

Ala Ala Leu His Lys Ala Ile Met Val Lys Gly Val Asp Glu Ala Thr
        50                  55                  60

Ile Ile Asp Ile Leu Thr Lys Arg Asn Asn Ala Gln Arg Gln Gln Ile
65                  70                  75                  80

Lys Ala Ala Tyr Leu Gln Glu Thr Gly Lys Pro Leu Asp Glu Thr Leu
                85                  90                  95

Lys Lys Ala Leu Thr Gly His Leu Glu Glu Val Val Leu Ala Leu Leu
            100                 105                 110

Lys Thr Pro Ala Gln Phe Asp Ala Asp Glu Leu Arg Ala Ala Met Lys
        115                 120                 125

Gly Leu Gly Thr Asp Glu Asp Thr Leu Ile Glu Ile Leu Ala Ser Arg
130                 135                 140

Thr Asn Lys Glu Ile Arg Asp Ile Asn Arg Val Tyr Arg Glu Glu Leu
145                 150                 155                 160

Lys Arg Asp Leu Ala Lys Asp Ile Thr Ser Asp Thr Ser Gly Asp Phe
                165                 170                 175

Arg Asn Ala Leu Leu Ser Leu Ala Lys Gly Asp Arg Ser Glu Asp Phe
            180                 185                 190

Gly Val Asn Glu Asp Leu Ala Asp Ser Asp Ala Arg Ala Leu Tyr Glu
        195                 200                 205

Ala Gly Glu Arg Arg Lys Gly Thr Asp Val Asn Val Phe Asn Thr Ile
    210                 215                 220

Leu Thr Thr Arg Ser Tyr Pro Gln Leu Arg Arg Val Phe Gln Lys Tyr
225                 230                 235                 240

Thr Lys Tyr Ser Lys His Asp Met Asn Lys Val Leu Asp Leu Glu Leu
                245                 250                 255

Lys Gly Asp Ile Glu Lys Cys Leu Thr Ala Ile Val Lys Cys Ala Thr
            260                 265                 270

Ser Lys Pro Ala Phe Phe Ala Glu Lys Leu His Gln Ala Met Lys Gly
        275                 280                 285
```

```
Val Gly Thr Arg His Lys Ala Leu Ile Arg Ile Met Val Ser Arg Ser
    290             295                 300

Glu Ile Asp Met Asn Asp Ile Lys Ala Phe Tyr Gln Lys Met Tyr Gly
305             310              315                 320

Ile Ser Leu Cys Gln Ala Ile Leu Asp Glu Thr Lys Gly Asp Tyr Glu
            325             330                 335

Lys Ile Leu Val Ala Leu Cys Gly Gly Asn
        340             345

<210> SEQ ID NO 2
<211> LENGTH: 24
<212> TYPE: PRT
<213> ORGANISM: Artificial Sequence
<220> FEATURE:
<223> OTHER INFORMATION: Synthetic (N-terminal domain of ANXA1)

<400> SEQUENCE: 2

Met Val Ser Glu Phe Leu Lys Gln Ala Trp Phe Ile Glu Asn Glu Glu
1               5                   10                  15

Gln Glu Tyr Val Gln Thr Val Lys
            20
```

CELL WITH SURFACE COATED WITH ANXA1 AND USE THEREOF

CROSS-REFERENCE TO RELATED APPLICATIONS

This application claims the benefit of Korean Patent Application No. 10-2013-0146224 filed on Nov. 28, 2013 in the Korean Intellectual Property Office, the entire disclosure of which is hereby incorporated by reference.

INCORPORATION BY REFERENCE OF ELECTRONICALLY SUBMITTED MATERIALS

Incorporated by reference in its entirety herein is a computer-readable nucleotide/amino acid sequence listing submitted herewith and identified as follows: One 3,675 bytes ASCII (Text) file named "718894_ST25.TXT" created Nov. 26, 2014.

BACKGROUND OF THE INVENTION

1. Field

Provided is a cell including a surface coated with ANXA1 (Annexin A1), a method of detecting an ANXA1-binding substance, and a method of preparing a cell including a surface coated with ANXA1.

2. Description of the Related Art

In general, to obtain an antibody against a specific antigen, a screening (bio-panning) method using phage displayed antibody library is commonly employed. To select an antibody specifically binding to an antigen in phage library, a method of detecting a positive antibody through solid-phase ELISA is generally employed. In some cases, the ELISA is performed using a cell expressing an antigen (i.e. Cell-ELISA). In the solid-phase ELISA, for an antibody which is selected thereby, it is necessary to confirm that it also binds to an antigen expressed on a cell. However, in the Cell-ELISA, such confirming step can be omitted.

ANXA1 (Annexin A1) belongs to the Annexin family of proteins. It has been known that ANXA1 is over-expressed in basal-like breast cancer thereby promoting cancer metastasis. For this reason, ANXA1 has emerged as an important target for anticancer drug development.

However, under in vitro conditions, only a small amount of ANXA1 is present on cell surface. Thus, when Cell-ELISA is performed, the ELISA signal generated from a non-purified antibody-expressing lysate in the initial screening step is too weak to determine whether the antibody is positive or not. For this reason, although an anti-ANXA1 antibody pool is obtained from library by bio-panning using various manners, it is difficult to select a positive one from any output pool through the use of the preexisting Cell-ELISA method.

Therefore, there is a need to develop a more effective method for detecting an ANXA1-binding substance.

BRIEF SUMMARY OF THE INVENTION

One embodiment provides a cell including a surface coated with ANXA1.

Another embodiment provides a method of preparing the cell including a surface coated with ANXA1. The method comprises providing a cell, and contacting the cell with ANXA1 in the presence of calcium ions, to prepare a cell having a surface coated with (having attached) ANXA1.

Another embodiment provides a composition for detecting an ANXA1-binding substance, wherein the composition includes the cell including a surface coated with ANXA1.

Still another embodiment provides a method of screening for or otherwise detecting an ANXA1-binding substance using the cell including a surface coated with ANXA1. The method comprises providing the cell having a surface coated with ANXA1; contacting the cell with a candidate substance, and measuring a reaction between ANXA1 and the candidate substance.

DETAILED DESCRIPTION OF THE INVENTION

A method of selecting an antibody by determining whether it binds to ANXA1, a protein expressed in a cancer cell, is provided.

To address problems of preexisting Cell-ELISA methods, a purified ANXA1 (exogenous ANXA1) is incubated with a cell in the presence of $Ca^{2+}$, thereby being displayed on, (i.e., attached to), a surface (outer surface) of the cell. As a result, ANXA1 is present on a surface of the cell at a high concentration. In such a manner, a signal intensity of Cell-ELISA generated by an ANXA1-binding substance (e.g., an antibody) contacted with the cell is increased at least four-fold as compared to the same substance contacted with a cell that is not incubated with exogenous ANXA1. Thus, a method of selecting an antibody binding to ANXA1 present on (e.g., displayed on or attached to) a cell surface by ANXA1 exogenous coating Cell-ELISA, is provided.

Figure 1:
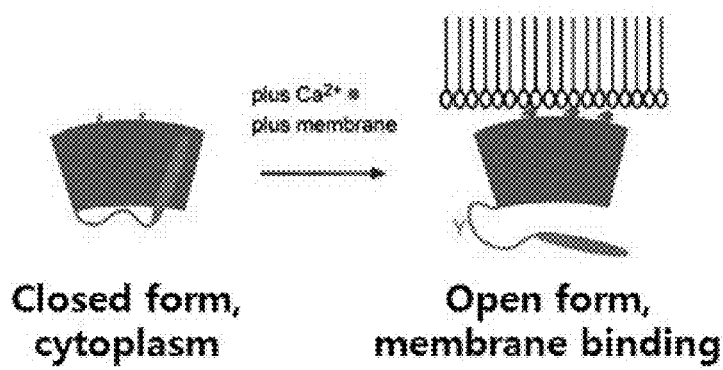
FIG. 1 is a schematic view showing a structure and a location change of cytosolic ANXA1 according to presence or absence of $Ca^{2+}$.

When extracellular calcium ions ($Ca^{2+}$) are present or extracellular concentration of calcium ions ($Ca^{2+}$) is increased (for example, the extracellular concentration of calcium ions may be from about 1 mM to about 5 mM), endogenous ANXA1 protein migrates away from cytoplasm and binds to cell membrane through calcium ion, thereby being exposed on cell surface (see FIG. 1). In a cancer tissue where calcium ions are present at a high concentrations, ANXA1 is displayed on cell surface as well as present in the cell, and thus, the ANXA1 displayed on cell surface can act as a cancer cell-specific antigen, similar to a receptor, capable of being targeted by specific binding of an antibody. If the amount of the ANXA1 protein which is exposed on cell surface is artificially increased, it can better facilitate detection of a substance capable of binding to the ANXA1 protein.

ANXA1 (Annexin I) belongs to Annexin family proteins which are $Ca^{2+}$-dependent phospholipid-binding proteins. The ANXA1 may be obtained from a mammal, such as a primate including a human, a monkey, etc., a rodent including a rat, a mouse, etc., and the like. For example, the Annexin may be at least one selected from the group consisting of human ANXA1 (e.g., NCBI Accession No. NP_000691.1, P49767, SEQ ID NO: 1, etc.), monkey ANXA1 (e.g., GenBank Accession No. AFH29166.1, etc.), mouse ANXA1 (UniProtKB/Swiss-Prot Accession No. P24551.3, etc.), and the like.

As used herein, the term "cell surface coated with ANXA1" refers to a cell surface to which or on which at least one ANXA1 molecule is attached and the term "coating" with respect to ANXA1 on a cell surface refers to attaching (or binding) at least one ANXA1 molecule to or on the cell surface.

Another embodiment provides a cell coated with ANXA1. More specifically the exterior cell surface is coated with ANXA1.

The ANXA1 may be an exogenous ANXA1, which is originated from the outside of the cell coated with ANXA1. That is, the exogenous ANXA1 refers not to an ANXA1 which is expressed in the individual cell to be coated with ANXA1 and present thereon, but to ANXA1 that is externally provided (i.e., originated from other than the individual cell to be coated with ANXA1). The exogenous ANXA1 may be one originated from (i.e., expressed in) a cell which is the same species (i.e., homogeneous) as the cell to be coated with ANXA1, or a cell that is a different species (i.e., heterogeneous) from the cell to be coated with ANXA1. The cell coated with an exogenous ANXA1 may include externally provided ANXA1 on its surface in addition to ANXA1 which is expressed in the cell and transported to the surface of the cell, thereby achieving a higher density of ANXA1 on the cell surface compared with that of a cell without a surface coated with exogenous ANXA1.

Another embodiment provides a method of preparing a cell with a cell surface coated with ANXA1. The coating of the cell surface with ANXA1 may be an exogenous ANXA1 coating of the cell surface as described herein.

The method of preparing a cell with a cell surface coated with ANXA1 may include: providing (obtaining) a cell, and contacting the cell with ANXA1 in the presence of calcium ions, to obtain a cell having a surface coated with ANXA1.

The coating of the cell surface with ANXA1 can be performed with a constant coating efficiency under a calcium ion concentration ($Ca^{2+}$) of about 1 mM to about 5 mM. However, a calcium ion concentration of more than about 5 mM exhibits an adverse effect on the cell condition, resulting in a decrease of the cell survival rate, thereby decreasing the efficiency of the coating of the cell surface with ANXA1. Therefore, calcium ions may be present at a concentration of about 5 mM or less, for example, from about 1 mM to about 5 mM or from about 1 mM to about 2 mM. In addition, to achieve a high coating efficiency, the exogenous ANXA1 may be added at a concentration from about 10 µg/ml to about 150 µg/ml, from about 30 µg/ml to about 120 µg/ml, from about 50 µg/ml to about 100 µg/ml, or from about 65 µg/ml to about 85 µg/ml, but not be limited thereto.

As described above, when the cell and exogenous ANXA1 are contacted to each other (e.g., suspended together, mixed together, etc.) under certain conditions (e.g., the presence of calcium ions, etc.), the surface of the cell (e.g., the outer surface) can be coated with exogenous ANXA1. The term "surface" as used herein refers to a surface of a membrane of a cell, particularly the outer (exterior) surface of the outer membrane of a cell.

The cell coated with exogenous ANXA1 prepared as above may have an increased density of ANXA1 on its surface as compared to the density of ANXA1 on the surface of the cell before being coated (contacted with exogenous ANXA1).

The cell with a surface coated with exogenous ANXA1 may be a cell obtained (isolated) from a mammal such as a primate including human, monkey, etc., a rodent including rat, mouse, etc., and the like. The cell may be a cell expressing or not expressing ANXA1. For example, the cell may be a cancer cell. The cell may be at least one selected from the group consisting of triple-negative breast cancer cell lines (e.g., MDA-MB-231, HCC1806, or MDA-MB-453), SNU-1, MCF7, HCT116, and any combination thereof, but not limited thereto.

The cell having a surface coated with ANXA1 includes ANXA1 on the surface at high concentration (for example, compared to a cell with no coating of exogenous ANXA1), thereby being capable of generating a signal at high intensity when a substance capable of binding to ANXA1 exists. Thus, the cell can be efficiently used in detecting and/or selecting an ANXA1 binding substance. The high concentration of ANXA1 on the surface may be achieved by applying (contacting) ANXA1 to the surface at a concentration from about 10 µg/ml to about 150 µg/ml, from about 30 µg/ml to about 120 µg/ml, from about 50 µg/ml to about 100 µg/ml, or from about 65 µg/ml to about 85 µg/ml, but not be limited thereto.

Another embodiment provides a composition for detecting an ANXA1 binding substance, wherein the composition includes the cell having a surface coated with ANXA1. Still another embodiment provides a kit for detecting an ANXA1 binding substance, wherein the kit includes the cell having a surface coated with ANXA1 and a means for measuring a reaction between ANXA1 and an ANXA1 binding substance. The means for measuring a reaction between ANXA1 and an ANXA1 binding substance may be a means (any reagent and/or device) used in a step of measuring a reaction between ANXA1 and an ANXA1 binding substance, as described below.

Another embodiment provides a method for screening (detecting) an ANXA1 binding substance using the cell having a surface coated with ANXA1. The method for screening an ANXA1 binding substance may include: providing a cell having a surface coated with ANXA1; contacting the cell with a candidate substance; and measuring a reaction between ANXA1 and the candidate substance. A reaction between ANXA1 and the candidate substance indicates that the candidate substance is an ANXA1 binding substance.

The cell having a surface coated with ANXA1 for use in the method is as described above with respect to other aspects of the disclosure.

The candidate substance may be any compound. For example, the candidate substance may be at least one selected from the group consisting of nucleic acids, peptides (e.g., oligopeptides, polypeptides, etc.), proteins, synthetic compounds, cultures or culture supernatants of microorganisms, natural ingredients obtained from plants or animals including marine organisms, plant extracts, animal tissue extracts, and any combination thereof. For instance, the oligopeptides or polypeptides may be used as an antigen-binding fragment of an anti-ANXA1 antibody or an aptamer against ANXA1, and the protein may be used as an anti-ANXA1 antibody.

The step of measuring a reaction (e.g., measuring binding) between ANXA1 and the candidate substance may be performed by any known method for measuring an interaction between a protein and another protein or other compound (e.g., small molecular compound, nucleic acid, peptide, protein (e.g., antibody), etc.). For example, the step of measuring may be performed by a detecting agent commonly used for measurement of enzyme reactions, fluorescent reactions, and/or luminescent reactions, and/or radiation detection. The detecting means (reagent and/or device) may be any reagent and/or device used in a conventional detection technique, which may include at least one selected from the group consisting of immunochromatography, immunohistochemistry, enzyme linked immunosorbent assay (ELISA), radioimmunoassay (RIA), enzyme immunoassay (EIA), fluorescence immunoassay (FIA), luminescence immunoassay (LIA), western blotting, microarray assay, and any combination thereof, but not be limited thereto.

A method of confirming binding between ANXA1 and a candidate substance for selecting a substance (e.g., an antibody, etc.) that specifically binds to ANXA1 present on a surface of a cell is provided. The method may facilitate detection of binding between a substance and ANXA1 on a cell by coating a surface of the cell with an exogenous ANXA1 by regulating $Ca^{2+}$ concentration, thereby increasing the detection sensitivity of Cell-ELISA. The method may be useful in developing anti-ANXA1 antibodies.

EXAMPLES

The following examples are intended merely to illustrate the invention and are not construed to restrict the invention.

Example 1

Preparation of a Cell Coated with Exogenous ANXA1

Figure 2:
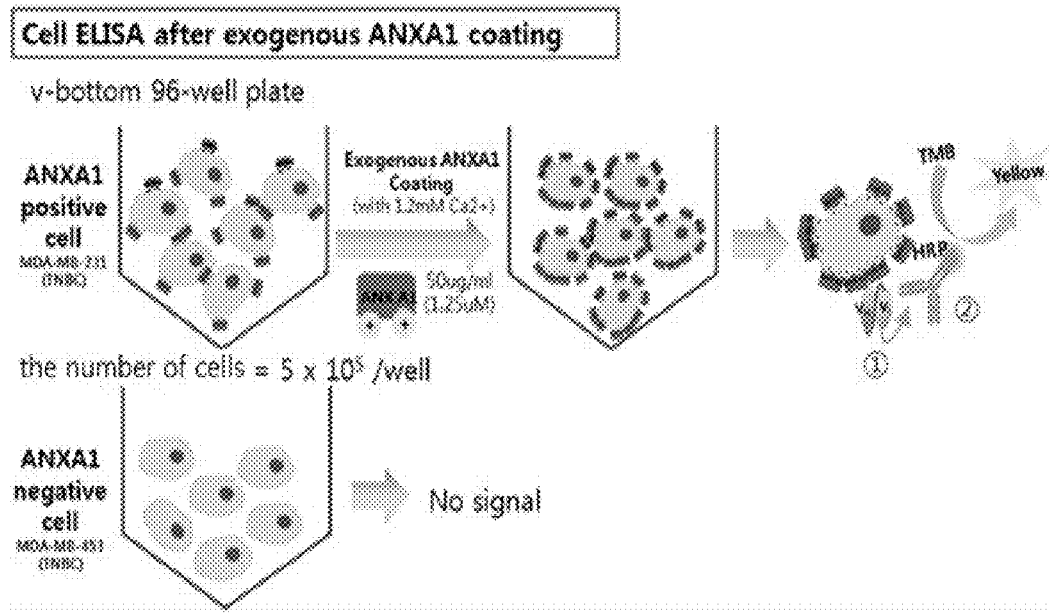
FIG. 2 is a schematic view showing a process of exogenous ANXA1 coating and Cell-ELISA utilizing the coating.

The process of preparing a cell coated with an exogenous ANXA1 is schematically illustrated in FIG. 2.

In particular, a cancer cell line MDA-MB-231 (ATCC) was incubated in 10% (v/v) FBS (Gibco) supplemented DMEM medium (Gibco) at 37° C. and 5% $CO_2$, and then incubated in 0.25% Trypsin-EDTA (Gibco) for 3 minutes, to separate adherent cells from the culture dish. The separated cells were washed with HBSS buffer (Invitrogen's 14025-092), and then $5 \times 10^7$ cells were suspended in 10 mL of HBSS buffer (which includes 1.2 mM $Ca^{2+}$) or 10 mL of a buffer including 50 mM Tris-HCl, 150 mM NaCl and 5 mM $CaCl_2$, to prepare a cell suspension (wherein all buffers used herein are in the condition of 4° C.).

A DNA fragment encoding the full-length ANXA1 protein (a total of 346 amino acids; Accession No. NP_000691.1; SEQ ID NO: 1) was incorporated into pET21b vector (Novagen) using restriction enzymes NdeI and XhoI (NEB, R0146S), and expressed in E. coli BL21 (Invitrogen) to produce a recombinant ANXA1 protein. The produced ANXA1 was added to the prepared suspension at the final concentration of 1.25 uM, and then incubated at 4° C. for 30 minutes. The suspension was centrifuged at 2000 rpm for 1 minute to precipitate the cells. The supernatant was removed, and 10 ml of fresh HBSS buffer (including 1.2 mM $Ca^{2+}$) or 10 ml of a fresh buffer including 50 mM Tris-HCl, 150 mM NaCl and 5 mM $CaCl_2$ was added to the precipitated cells to resuspend the cells, thereby producing ANXA1 coated cells.

For the produced ANXA1 coated cell, the successful coating of ANXA1 and the level of coated ANXA1 were examined. In particular, cancer cell line MDA-MB-231 (ATCC) was incubated in DMEM medium (Gibco) supplemented with 10% (v/v) FBS (Gibco) at 37° C. and 5% $CO_2$, and then incubated in 0.25% Trypsin-EDTA (Gibco) for 3 minutes, to separate adherent cells from the culture dish. The separated cells were washed with HBSS buffer (Invitrogen's 14025-092), and then $4 \times 10^6$ cells were suspended in 10 mL of HBSS buffer (which includes 1.2 mM $Ca^{2+}$), to prepare a cell suspension.

ANXA1 was added to 0.5 ml of the cell suspension, so that the final concentration of ANXA1 reached 1.25 uM. The cell suspension was subsequently incubated at 4° C. for 30 minutes. The rest of the cell suspension (i.e. the suspension not containing added ANXA1) was incubated at 4° C. for 30 minutes as well. Each of the cell suspensions was centrifuged at 2000 rpm for 1 minute to precipitate the cells, treated with 0.5 mL of anti-ANXA1 antibody (BD Bioscience, 610067) which is diluted to the ratio of 1/10 in HBSS buffer (including 1.2 mM $Ca^{2+}$), and incubated at 4° C. for 1 hour. The obtained resultant was centrifuged again at 2000 rpm for 1 minute to precipitate the cells, and the cells were re-suspended by adding 0.5 ml of HBSS buffer thereto. The obtained suspension was treated with FITC-tagged anti-mouse IgG (Jackson ImmunoResearch, 115-096-146) which is diluted to the ratio of 1/100 in 0.5 mL of HBSS buffer (including 1.2 mM $Ca^{2+}$), and then, washed with HBSS buffer.

The amount of Annexin A1 present on the surface of the cancer cell was measured as a FITC fluorescence intensity of the secondary antibody which is measured using FACScantoII instrument (BD) and Flowjo software. To prevent the treated proteins from being internalized into a cell, all incubations of cells together with ANXA1 protein and all antibodies were performed at 4° C.

Figure 3:
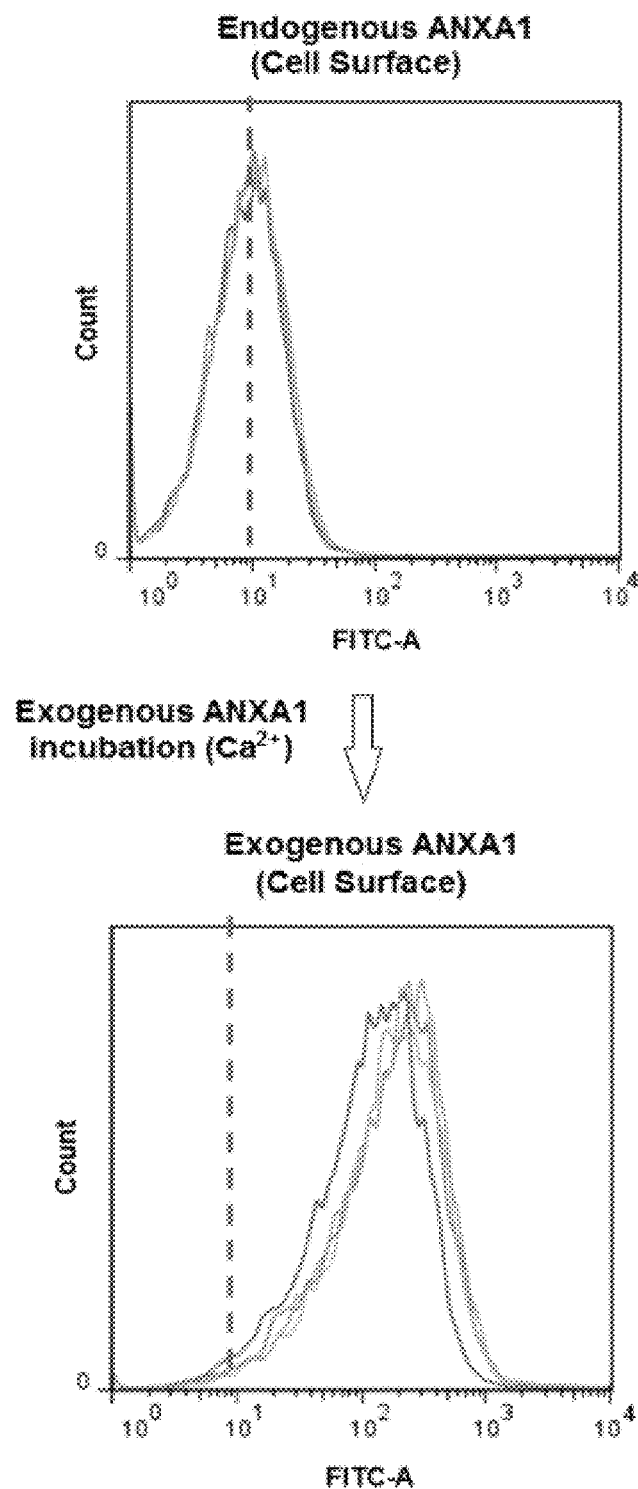
FIG. 3 provides two graphs showing FACS results obtained using ANXA1-coated cells and ANXA1-binding scFv.

The obtained results are displayed in FIG. 3. As shown in FIG. 3, MDA-MB-231 having a surface coated with exogenous ANXA1 exhibits increased ANXA1 signal on the surface of the cell, indicating the increase of the amount of ANXA1 on the surface of the cell. The results indicate that the exogenous ANXA1 is further deposited on (i.e. bound to) the surface of the obtained MDA-MB-231 cell in addition to originally existing ANXA1 thereon.

Example 2

Preparation of ANXA1 Binding scFv Antibody

To select an Annexin A1 (ANXA1) specific antibody in the scFv form, a process of biopanning using an antibody phage library was performed, to obtain an ANXA1-binding scFv pool.

In particular, a DNA fragment encoding the full-length ANXA1 (a total of 346 amino acid; Accession No. NP_000691.1) was incorporated into pET21b vector (Novagen) using restriction enzymes NdeI and XhoI (NEB, R0146S), expressed in E. coli BL21 (Invitrogen), purified using a His tag, and produced in a biotin-attached form using a biotinylation kit (Pierce).

Each of N-terminal peptide (amino acid sequence: MVSEFLKQAWFIENEEQEYVQTVK (SEQ ID NO: 2); which is the region from $3^{rd}$ to $26^{th}$ positions of SEQ ID NO: 1, and will be cleaved by in vivo cleavage) of the biotin-attached ANXA1 and full length ANXA1 protein was attached to streptavidin-fixed magnetic beads (Invitrogen), and mixed with $10^{12}$ pfu of scFv-displaying phage library (prepared referring to "Construction of a large synthetic human scFv library with six diversified CDRs and high functional diversity. Moll. Cells 27, 225-235, Feb. 28, 2009"). The mixture was reacted at 4° C. for 30 minutes, allowing for binding. The obtained resultant was washed with HBSS(+) (Gibco) to remove non-binding scFv. A biopanning (Ehrlich G K, Berthold W, and Bailon P. *Phage display technology. Affinity selection by biopanning*. Methods in molecular biology. 2000. 147:195-208) for recovering ANXA1-binding scFv only was performed repeatedly three (N-terminal peptide of ANXA1) or four times (full-length ANXA1 protein). Through the process, a scFv pool specifically binding to N-terminal peptide of ANXA1 or full length ANXA1 protein was obtained.

To analyze each scFv pool specifically binding to ANXA1, ER2537 (New England Biolabs Inc.) which is an *E. coli* strain transfected with the phage clone, was incubated, and then a cytoplasm fraction was separated using 20% (w/v) sucrose solution, to obtain scFv displayed on the surface of the phage.

Example 3

Verification of Binding Specificity of scFv Using an ANXA1 Expressing Cell

The binding specificity of the selected scFv in the cytoplasm fraction to ANXA1 was verified by a cell-based ELISA using ANXA1-abundant MDA-MB-231 (ATCC).

In particular, each of cancer cells, MDA-MB-231 (ATCC; ANXA1 expressing cell) and MDA-MB-453 (ATCC; ANXA1 non-expressing cell), was incubated in DMEM medium (Gibco) supplemented with 10% FBS (Gibco) at 37° C. and 5% $CO_2$ for at least one day. Each of the incubated MDA-MB-231 and MDA-MB-453 was treated with trypsin (0.25% (w/v) Trypsin-EDTA; Gibco) and then washed with HBSS.

$5 \times 10^7$ cells of MDA-MB-231 were suspended in 10 mL of a mixture of HBSS (Gibco, 14025-092) and 10% FBS (Gibco) buffer (hereinafter, referred to as "HBSS(+)F"; including 1.25 mM calcium ions), $5 \times 10^7$ cells of MDA-MB-453 were suspended in 10 mL of a mixture of HBSS (Gibco, 14175-095) and 10% FBS (Gibco) buffer (hereinafter, referred to as "HBSS(−)F"; including neither calcium ions nor magnesium ions), and the obtained suspensions were provided in 50 ml conical tube at 4° C.

Referring to Example 1, the provided MDA-MB-231 cells were treated with ANXA1 at the final concentration of 50 ug/ml (1.25 µM), and then incubated at 4° C. for 30 minutes. The MDA-MB-453 cells were incubated at 4° C. for 30 minutes with no ANXA1 treatment. Each of MDA-MB-231 and MDA-MB-453 cells was washed once with 100 ul/well of HBSS(+)F or HBSS(−)F buffer, and suspended in HBSS (+)F or HBSS(−)F buffer. The prepared cell suspension was added onto Corning 96 Well Clear V-Bottom TC-Treated Microplate (Corning's 3894) so that the cell amount reaches $5 \times 10^5$ cells per a well. The cell suspension was centrifuged at 2000 rpm for 1 minute to precipitate the cell in 96-well, and buffer was removed.

To the resultant, each *E. coli* cell fraction solution obtained from the individual phage clone was added at the amount of 50 ul. Then, MDA-MB-231 cell line was incubated in the presence of 5 mM $Ca^{2+}$ at 4° C. for 90 minutes, and MDA-MB-453 cell line was incubated with no $Ca^{2+}$ at 4° C. for 90 minutes. Each of the incubated cell line was washed twice with HBSS(+)F or HBSS(−)F buffer. Thereafter, HA tag binding anti-HA-HRP secondary antibody (Santa Cruz) binding to HA tag present at terminal region of the scFv was diluted in HBSS(−)F buffer to the ratio of 1/200, and 50 ul of the diluted secondary antibody was added to each cell line, to be allowed to bind the cells. To each resultant, Super AquaBlue ELISA substrate solution (eBioScience) was added at the amount of 150 ul, and 30 minutes after, the absorbance was measured at 405 nm using HRP of the secondary antibody.

Figure 4:
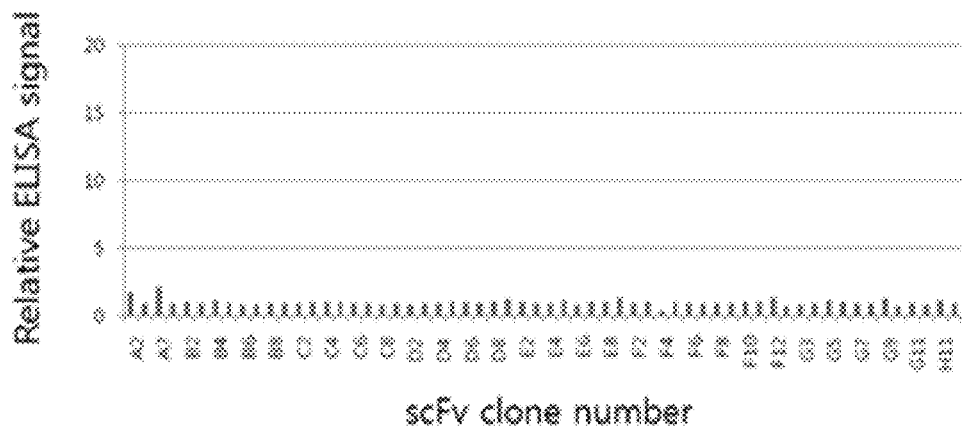
FIG. 4 provides two graphs showing the ELISA signal intensity of Cell-ELISA using ANXA1-coated cells compared with that of preexisting Cell-ELISA, wherein upper graph shows the ELISA signal intensity of preexisting Cell-ELISA using non-ANXA1-coated cells and lower graph shows the ELISA signal intensity of Cell-ELISA using ANXA1-coated cells.
Figure 4:
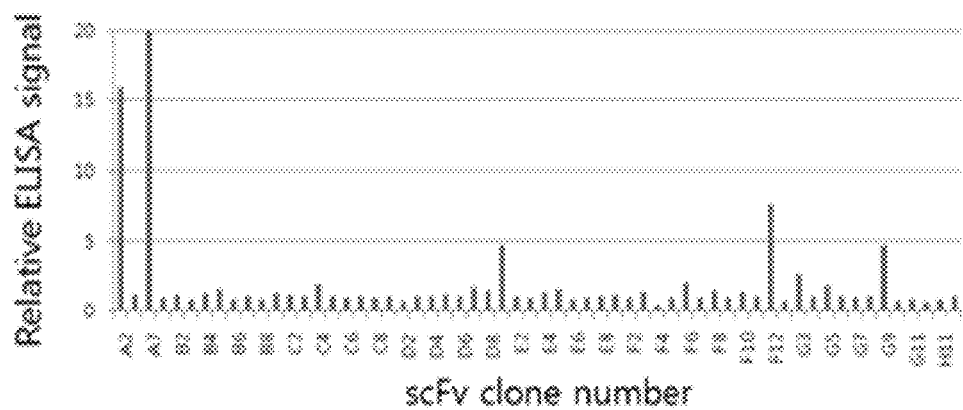

The obtained results are displayed in FIG. 4. In FIG. 4, the lower graph (2) illustrates results obtained by the above method, and the upper graph (1) illustrates results obtained by the above method except the step of coating MDA-MB-231 cell line with ANXA1 (i.e., the step of incubating MDA-MB-231 cell line together with ANXA1 at the final concentration of 50 ug/ml (1.25 µM) at 4° C. for 30 minutes). In FIG. 4, the relative ELISA signal of Y axis refers to A/B value, wherein 'A' is a cell-ELISA result (absorbance at 405 nm) of exogenous ANXA1 coated (1) or non-coated (2) MDA-MB-231 cell and 'B' is a cell-ELISA result (absorbance at 405 nm) of MDA-MB-453 cell (ANXA1 negative cell) which does not express ANXA1, and wherein 'A' and 'B' were measured for each cell fraction (X axis: the *E. coli* cell fractions obtained from the phage clones were named from A1).

As shown in FIG. 4, although MDA-MB-231 cell expresses ANXA1, MDA-MB-231 cell (1) without being coated with exogenous ANXA1 exhibits very slight binding signal between the scFv clones and ANXA1, and thus, it is difficult to exactly determine which scFv effectively binds to ANXA1. However, in exogenous ANXA1 coated MDA-MB-231 cell (2), scFv clones A2, A7, D8, F12, and G9 exhibit considerably intensive binding signal to ANXA1, compared with other clones, indicating that the scFv clone capable of effectively bonding to ANXA1 can be exactly and easily selected using exogenous ANXA1 coated cells.

It should be understood that the exemplary embodiments described herein should be considered in a descriptive sense only and not for purposes of limitation. Descriptions of features or aspects within each embodiment should typically be considered as available for other similar features or aspects in other embodiments.

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and "at least one" and similar referents in the context of describing the invention (especially in the context of the following claims) are to be construed to cover both the singular and the plural, unless otherwise indicated herein or clearly contradicted by context. The use of the term "at least one" followed by a list of one or more items (for example, "at least one of A and B") is to be construed to mean one item selected from the listed items (A or B) or any combination of two or more of the listed items (A and B), unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

What is claimed is:

1. A method for screening for an ANXA1 binding substance that binds to ANXA1 on a surface of a cancer cell, the method comprising
providing the cancer cell having a surface coated with ANXA1, wherein the ANXA1 is exogenous to the cancer cell;
contacting the cancer cell with a candidate substance,
measuring a reaction between ANXA1 and the candidate substance, and
selecting the candidate substance as the ANXA1 binding substance that binds to ANXA1 on the surface of the cancer cell, when the reaction between ANXA1 and the candidate substance is confirmed,
wherein the cancer cell is a triple-negative breast cancer cell line, SNU-1, MCF7, HCT116, or a combination thereof.

2. The method of claim 1, wherein the candidate substance is at least one selected from the group consisting of nucleic acids, peptides, proteins, synthetic compounds, cultures of microorganisms, natural ingredients obtained from plants or animals, plant extracts, animal tissue extracts, and any combination thereof.

3. The method of claim 1, wherein the ANXA1 is a human ANXA1.

* * * * *